United States Patent [19]

Demuth et al.

[11] Patent Number: 5,123,144
[45] Date of Patent: Jun. 23, 1992

[54] METHOD AND APPARATUS FOR ESTABLISHING WHETHER FIBER MATERIAL IS CONTAMINATED WITH FOREIGN OBJECTS

[75] Inventors: Robert Demuth, Nuerensdorf; Jürg Faas, Dinhard, both of Switzerland

[73] Assignee: Maschinenfabrik Rieter AG, Winterthur, Switzerland

[21] Appl. No.: 564,852

[22] Filed: Aug. 9, 1990

[30] Foreign Application Priority Data

Aug. 9, 1989 [CH] Switzerland .......................... 3926346

[51] Int. Cl.⁵ .......................... D01B 3/04; G01N 25/72
[52] U.S. Cl. .................................... 19/65 A; 358/105; 310/336; 374/5
[58] Field of Search ...................... 358/105, 106, 107; 310/336; 374/5; 19/65 A

[56] References Cited

U.S. PATENT DOCUMENTS

| | | | |
|---|---|---|---|
| 3,750,461 | 8/1973 | Felix | 73/67.1 |
| 4,095,475 | 6/1978 | Buckeley | 73/628 |
| 4,167,803 | 9/1979 | Teichmann | 19/0.2 |
| 4,171,262 | 10/1979 | Lattmann et al. | 209/555 |
| 4,200,921 | 4/1980 | Buckley | 367/87 |
| 4,354,132 | 10/1982 | Berburgh et al. | 310/336 X |
| 4,439,049 | 3/1984 | Hoogemdroone et al. | 374/5 X |
| 4,594,897 | 6/1986 | Bautz | 310/336 X |
| 4,634,290 | 1/1987 | Rosencwaig et al. | 374/5 |
| 4,731,663 | 3/1988 | Kovalchik et al. | 358/106 X |
| 4,758,888 | 7/1988 | Lapidor | 358/106 |
| 4,760,270 | 7/1988 | Miller | 358/106 X |
| 4,760,444 | 7/1988 | Nielson et al. | 358/106 X |
| 4,805,266 | 2/1989 | Leifeld et al. | |
| 4,820,932 | 4/1989 | Miller | 358/106 X |
| 4,826,326 | 5/1989 | Reynolds et al. | 374/5 |
| 4,839,943 | 6/1989 | Leifeld | |
| 4,854,171 | 8/1989 | Hergeth | |
| 4,858,277 | 8/1989 | Pinto et al. | |
| 4,863,268 | 9/1989 | Clarke et al. | 358/106 X |
| 4,951,223 | 8/1990 | Wales et al. | 358/107 X |

FOREIGN PATENT DOCUMENTS

| | | |
|---|---|---|
| 000033 | 12/1978 | European Pat. Off. |
| 285602 | 3/1988 | European Pat. Off. |
| 3708188 | 9/1988 | Fed. Rep. of Germany |
| 2556837 | 6/1985 | France |
| 2095828 | 10/1982 | United Kingdom |
| 2202943 | 10/1988 | United Kingdom |

OTHER PUBLICATIONS

European Search Report labelled RS 85060 CH.

*Primary Examiner*—Werner H. Schroeder
*Assistant Examiner*—John J. Calvert
*Attorney, Agent, or Firm*—Burns, Doane, Swecker & Mathis

[57] ABSTRACT

A method and an apparatus for establishing whether fiber material is contaminated with foreign objects is characterized in that for the finding of foreign objects in the form of foreign fibers and pieces of foil, for example packaging remnants such as jute sack remnants, plastic foil remnants, cords or bands, rags or cleaning scrim, the fiber material delivered in bales is investigated during bale opening. The investigation takes place by scanning the surface of at least some of the layers of fiber material exposed during the bale opening, and the degree of the contamination with the scanned foreign objects is retained and is stored in association with the particular bale which has been scanned.

38 Claims, 3 Drawing Sheets

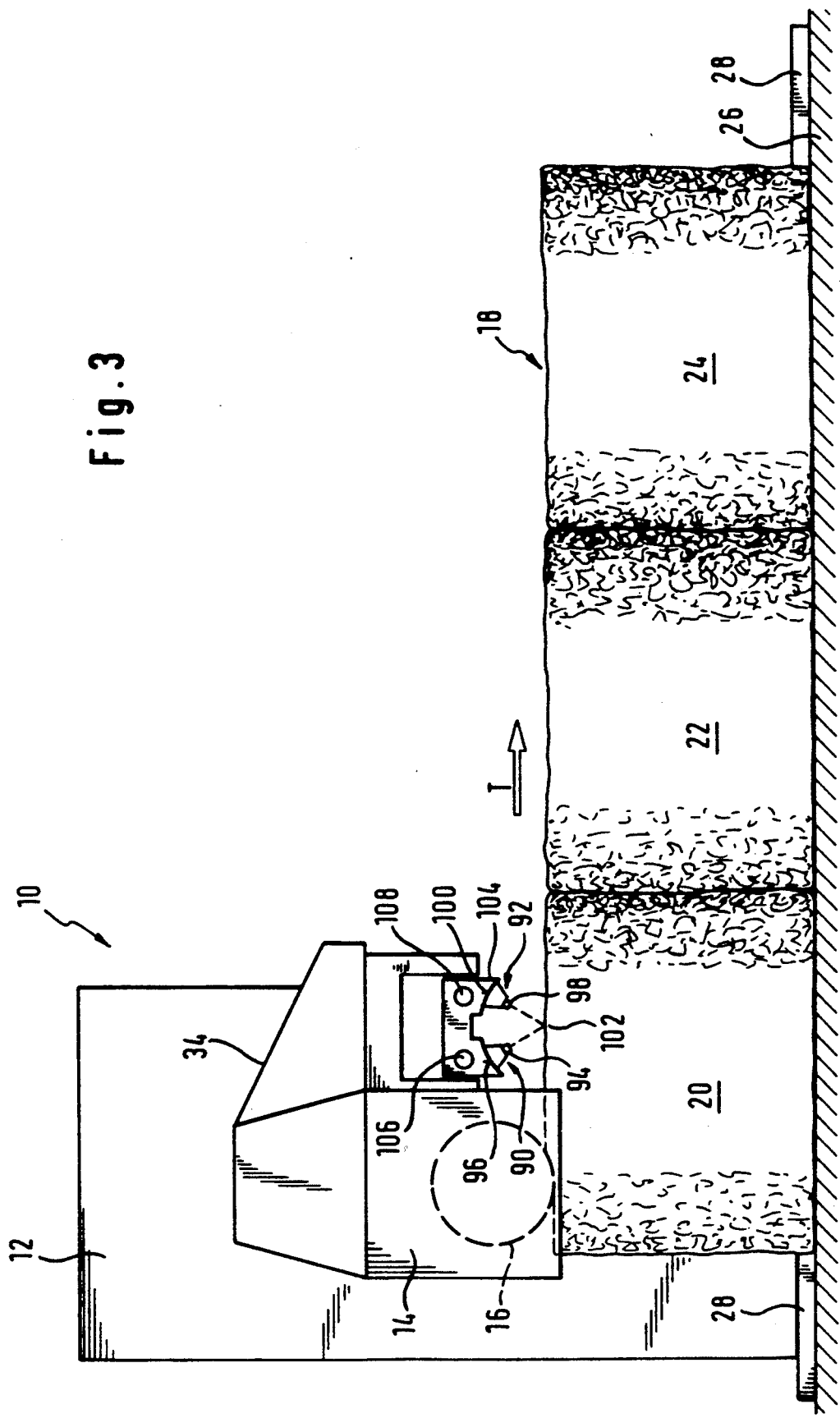

METHOD AND APPARATUS FOR ESTABLISHING WHETHER FIBER MATERIAL IS CONTAMINATED WITH FOREIGN OBJECTS

BACKGROUND OF THE INVENTION

The present invention relates to a method or to an apparatus for establishing whether fiber material is contaminated with foreign objects.

Foreign objects in cotton are understood to include:
a) dirt and contamination;
b) minerals, for example stones;
c) metal parts;
d) foreign fibers and foils which, for example, include packaging remnants such as jute sack remnants, plastic foil remnants, cords and bands, rags or cleaning scrim.

Currently, foreign fibers and foreign foils are the chief cause of difficulties in spinning mills, since for this category of foreign objects there is still no tested separation device. The other forms of foreign objects, for example dirt and contamination, minerals and metal parts can be satisfactorily separated out with the present state of the art, even if this is in many cases associated with a simultaneous and undesired loss of fibrous material. If, however, foreign fibers or foil remnants are present then these lead to negative effects in the spinning mill. For example, poor running behavior of the spinning machines occurs as do increased thread breakage rates, and yarn faults arise in the form of weak positions, thin and thick positions and color errors. Foreign fibers can also lead to damage to the point clothing in cleaning machines, although this is more seldom.

Various proposals have already been made as to how one can separate out the foreign fibers. Most proposals aim at splitting the fiber flocks and the foreign fibrous substances up into a stream of fibers, locating the foreign fibers and then separating out part of the fiber stream. As an example attention is directed to DE OS 36 44 535. A more recent, not yet prior published proposal of this kind can be found in the patent application filed by Maschinenfabrik Rieter AG in Switzerland on Oct. 11, 1988 with the title "Recognition of Foreign Material in Textile Fibres" Swiss patent application No. 03 803/88-4 corresponding to U.S. application Ser. No. 07/419,709 filed Oct. 11, 1989 of the present applicants' (EP - Publication Nr. 0364786). EP OS 285 602 also describes the recognition and separation out of foreign objects with a loose fibrous material having a flock weight of $10^{-1}$ to $10^{-3}$ g/flock, which is obtained after bale opening.

SUMMARY OF THE INVENTION

The present invention is based on an object of considering the problem of foreign fibers from a totally different direction whereby instead of making complex attempts to fully automate separation of the foreign fibers, a method or an apparatus is provided which makes it possible to establish the contamination of the fiber bales with foreign fibers, so that upon establishing an unacceptable degree of contamination of the fiber bales with foreign fibers a price rebate can be achieved from the supplier.

In other words, the invention seeks to attack the problem at its roots by providing the preconditions for recognizing bales which are heavily contaminated with foreign fibers, with the object of being able to attain some recourse against the cotton supplier and/or dealer, so as to be able to return the faulty bales which have been supplied or to achieve a reduction in delivery price, whereby the corresponding demands placed on the dealer or cotton supplier should lead to measures which address the cause of the contamination at the source of the contamination.

In other words, it is assumed that as a result of the foreign fibers no "fatal" consequential faults such as damage to the installation will occur in the spinning mill but rather that the foreign fibers will lead to a lower quality of the yarn which could be compensated for by a price rebate for the raw material.

Furthermore, the present invention provides the precondition for enabling the cotton suppliers themselves to investigate the cotton material which is supplied, at least by random sampling, to establish the level of contamination by foreign fibers and foreign foils.

In order to satisfy the object underlying the invention it is proposed method-wise, that for the finding of foreign objects in the form of foreign fibers and pieces of foil, for example packaging remnants such as jute sack remnants, plastic foil remnants, cords or bands, rags or cleaning scrim, the fiber material delivered in the bales is investigated during bale opening; that the investigation takes place by scanning the surface of at least some of the layers of fiber material exposed during the bale opening; and that the degree of the contamination with the scanned foreign objects is retained and is stored in association with the particular bale.

From the apparatus viewpoint the invention provides that the apparatus is a scanning device which can be mounted on a traveling bale opening machine, or on a structure disposed adjacent to a fixed bale opening machine, to scan the surface of the individual bales which is laid free layer-wise during bale opening to determine foreign objects in the form of foreign fibers and pieces of foil, for example packaging remnants such as jute sack remnants, pieces of plastic foil, cords or bands, rags or cleaning scrim, and also a storage means for storing the result of scanning the respectively associated bale.

With these proposals it is recognized that the typical foreign fiber contamination will come to light at the surface of the bale during bale opening with the layer-wise build-up, the individual bales making it possible to carry out a random sample check of the individual bales to establish their content of foreign fibers. Furthermore, an unambiguous association of the contamination that is found with a particular bale is possible during bale opening, so that one can provide a problem free piece of evidence for later complaints.

It is indeed already known from DE OS 34 36 498 to find foreign objects in the form of metallic parts such as iron bands and pieces of wire, tools and the like in the textile fiber bales using foreign object seeking devices, however this proposal aims at finding the foreign objects which are present in the interior of the fiber bale by radiation, such as X-ray radiation which penetrates the fiber bales, and then removing them. The specification is not however concerned with the finding of foreign fibers and also does not exploit the opportunity, as does the present invention, of detecting the foreign fibers which can be found at the exposed surface of the bales.

The present invention furthermore recognizes that the degree of contamination can be quoted by the number of the foreign objects scanned and/or by the extent of the foreign and/or by the color of the foreign objects and/or by a value which corresponds to these parameters.

In a bale opening machine with a tower which is movable along a row of bales and which carries an opening member accommodated in an arm of the bale opening machine, the scanning of the exposed surface can be carried out by means of a scanning device which is mounted on the tower or arm of the bale opening machine preferably in the opening direction in front of the opening member accommodated in the arm. The mounting of the scanning means in the opening direction in front of the opening member has the advantage that a particularly stationary surface is present here, so that disturbance of the scanning by the operation of the opening member can be avoided. In a bale opening machine which is stationary, and in which material is removed from bales which are advanced in the direction of the bale opening machine, the scanning means can be mounted on fixed structure, although it could here also be mounted on the housing of an opening member which is moved to and fro.

The scanning means preferably operates on an electro-optical basis. By way of example the process can be so laid out that the surface of the exposed layers of fibrous materials are photographed with a video camera and the obtained video images are stored as evidence for the contamination of the bale. This storage can take place in the simplest case in the form of a video film which also carries an identification of the bale which is being opened, for example in the form of a bar code. It is namely already known to provide fiber bales with bar codes which contain particulars of the origin of the bale and the fiber characteristics. This bar coding could be placed on the bale for the purpose of reliable recognition of the bale during the first pass over the surface of the bale, or on the bale opening machine in the immediate vicinity of the bale, and could be recorded by the video camera together with the bale surface. The video film can also be straightforwardly provided with a commentary so that in this way the statements relating to the origins of the particular bales are also established in troublefree manner.

It is not necessary to view all video films in order to recognize the presence of contamination in the bales with the human eye. Instead of this the video films can be temporarily stored until the corresponding fiber material has been processed into yarn or woven material. A reason for looking at the stored video films only arises if an increased level of faults is determined during yarn manufacture. Here, the present invention provides assistance since one preferably proceeds, in accordance with the invention, in such a way that the subsequent manufacturing process in which the fibrous material is processed into yarn is so carried out that an association is present between the fibrous material at the various stages of processing and the particular fiber bales from which it originates, whereby, on finding an increased number of faults during yarn manufacture the video recording associated with the relevant bales can be intentionally checked by an operator in order to secure evidence of contamination with modest effort. Instead of storing only video films, the possibility also exists of imaging the surface of the exposed fiber layers with the video camera and processing and evaluating the so obtained video signals to form foreign object contamination signals.

During video recording one can prepare video recordings from the entire surface of each layer during opening of the fiber material layer. It is however also possible to prepare video recordings only during some of the passes of the bale opening machine, for example each time layers of a specific thickness have been removed, for example each time when the individual bales have been shortened by 10 cm. This also embraces the recognition that it is not necessary to recognize 100% of the contamination in specific bales, but rather only a fraction of the foreign fiber contamination that is present since, on this basis, one can also provide statistics for the degree of contamination, and thus also a basis for the comparison of individual bales.

A particularly preferred method variant is characterized in that at least the strip of the surface photographed by the video camera, or the corresponding surface region, is at least substantially uniformly illuminated with diffuse light. This method variant ensures that good contrast can also be obtained during video recordings. The illumination preferably takes place by means of a flourescent tube arranged at the focal line of a concave mirror which extends over the width of the bales, for example a cylindrical mirror or a parabolic mirror, with the fluorescent tube or the focal line of the elongate concave mirror lying transverse to the bale and in a horizontal plane.

When the fluorescent tube has a spectral radiation distribution which extends from at least approximately 400 to approximately 700 nm, and preferably a spectral radiation distribution which extends still further into the infrared region and eventually also still further into the UV-region, then the video camera can be a conventional video camera with recording means for different spectral regions. For example the spectral regions blue, green and red, and the video signals for the three recording devices can be separately evaluated. A whole multitude of possibilities is available for the evaluation of the video signal or of the video signals. For example, one can assume that with uniform illumination of a surface consisting of pure cotton fibers the latter will be present as a uniformly bright background so that all fluctuations of the amplitude of the video signal (or of the video signals) outside of a specified threshold range point to contamination. The area of the contamination can also be determined from the number of the affected "pixels" in the video image, whereby the degree of the contamination can be verified and quantified.

By investigation of the video signals in different color regions the different characteristics of the different possible contaminations in different spectral regions is exploited in order to make this contamination visible.

A further possibility for increasing the degree of efficiency of the scanning means lies in providing polarization filters which serve to change or to specify the state of polarization of the light irradiated from the fluorescent tube and/or picked up by the video camera.

The scanning of the bale surface can also take place with means other than video camera recordings. For example one can, effect the scanning of the exposed surface of the fiber material layers by means of an ultrasonic scanning device carried by the opening machine. Furthermore, the possibility exists of carrying out the method of the invention in such a way that the exposed surface of the bale is heated up, for example with infrared radiation or with micro-wave energy, in order to prepare a thermal image of the surface from which the degree of contamination can be found, for example by the proportions of the area of the image having a temperature which is increased or reduced relative to the fibrous material.

A particularly important embodiment relates to the finding of larger foreign objects, wherein a further possibility exists of separating them out, optionally after interrupting the opening process.

Further advantageous forms of the apparatus of the invention will be described in the detailed description of preferred embodiments.

BRIEF DESCRIPTION OF THE DRAWINGS

Other objects and advantages of the present invention will become more apparent from the following detailed description of preferred embodiments as described in conjunction with the accompanying drawings in which:

FIG. 3 is a further side view of a bale opening machine in accordance with FIG. 1, however with a heat source and a scanning means which generates a thermal image.

DETAILED DESCRIPTION OF THE PREFERRED EMBODIMENTS

Figure 1:
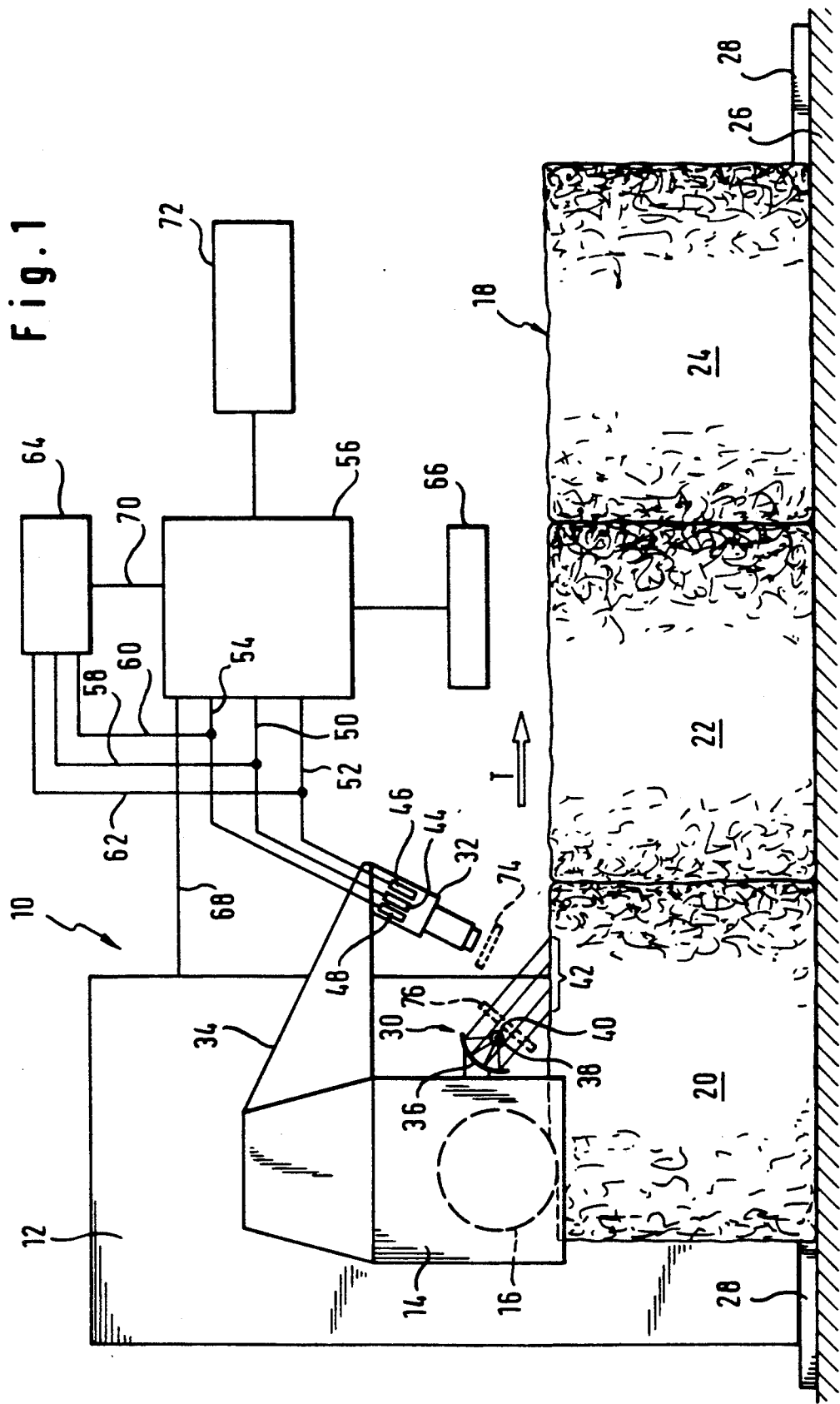
FIG. 1 is a side view of a bale opening machine with a tower which is movable along a row of bales and a video camera which is mounted on the tower or on the arm of the bale opening machine.

FIG. 1 shows a bale opening machine 10 with a tower 12 which has an arm 14 at one side in which a rotatable opening member 16 is accommodated, for example a rotor equipped with toothed discs. The bale opening machine 10 serves for opening a row of bales 18, which in this example consists of three bales 20, 22 and 24. These bales are arranged alongside one another on the floor and the tower 12 can travel via wheels (not shown) along the rails 28 mounted on the floor 26, with the opening member 16 opening the row of bales 18 layer-wise in a known manner. The flock material which is removed and which is simultaneously opened by the opening member 16 is brought into a transport duct provided in the upper part of the opening arm 14 by means of which it is supplied to a cleaning machine provided after the bale opening machine.

In the bale opening machine shown in FIG. 1 opening is only carried out in one direction, namely in the arrow direction T. An illuminating means 30 and a video camera 32 are mounted in front of the arm 14. The video camera 32 is carried from the arm 14 by means of a stable structure 34.

As can be seen from FIG. 1 the illuminating means comprises an elongate concave mirror 36 which extends over the entire width of the row of bales, i.e. perpendicular to the plane of the drawing in FIG. 1. The concave mirror 36 is a cylindrical mirror with a focal line 38 which likewise extends transversely over the width of the row of bales 18 and which lies in a horizontal plane. A fluorescent tube, for example a "Lumilux" tube of the Osram company, type tw 19 is arranged coaxial to the focal line. The fluorescent tube 40 uniformly illuminates a region 42 of the bale surface both directly and also indirectly via the concave mirror 36, with this region likewise extending transversely over the entire width of the row of bales or of the individual bales. The video camera 32 is directed and focussed into the illuminated region 42. This camera has, as is customary with color video cameras, three picture tubes which respectively record light from the blue, green and red parts of the spectrum. The strong illumination makes the surface of the bale row self-luminous. The three video color signals from the three picture tubes 44, 46 and 48 are supplied via respective lines 50, 52 and 54 to a computer 56 after being converted into digital signals. Furthermore, these video signals are passed via lines 58, 60 and 62 to a known video recording device 64, and the device 64 prepares a video cassette which represents a permanent record of the surface of the bale row exposed during bale opening.

A keyboard 66 makes it possible for an operator to feed into the computer particulars of the individual bales 22 to 24 arranged in the row 18, so that the computer can produce a problem free association of the video recording signals on the lines 50, 52 and 54 with the individual bales. For this purpose the computer 56 also receives signals via the line 68 which give the instantaneous position of the tower along the row of bales 18. The computer 56 also feeds particulars corresponding to the signals 68 and the inputs at the keyboard 6 to the video recording unit 64 via the line 70 so that on the video film a trouble free association is given between the recordings and the individual bales. These particulars can for example be stored on the sound track of the video cassette. The computer 56 is also able to process the video signals which it receives so that particulars of the degree of contamination in the bale surface can be obtained from the processed signals and these particulars can then be printed out, for example via a printer 72.

The processing of the video signals to signals which represent the degree of contamination can take place in many diverse ways. For example one can assume that with a unitary type of cotton the surface will have a uniform color and scattering characteristic. Accordingly the video signals with high quality bales without contamination must have a substantially constant amplitude which is proportional to the strength of the illumination. Accordingly, threshold values can be set in the computer 56, for example via the keyboard 66, and only those video signals are taken into account where the signal amplitude lies below or above the specified threshold region. As the information of a video signal automatically contains information for each pixel, and each pixel in turn corresponds to a precise unit of area of the illuminated bale surface, it is possible, by analyzing the number of pixels where the signal amplitude lies outside of the threshold value range, to make statements concerning the areal extent of the contamination in the opened layer, and the size of this area can be used as a measure for the degree of the contamination. Foreign fiber materials of different colors can be recognized better if one investigates the surface in three different color ranges, and this is preferably done.

It is also possible to investigate the video signals to see in which adjoining pixels of an image an amplitude is present which deviates from average pixel amplitude, and only to process those signals further in which a plurality of interconnected pixels with disturbed signals can be found. Here one assumes that the areal extent of the contaminations must exceed a certain level in order to be recognized as a contamination. Groups of pixels having amplitudes different from the average are therefore regarded as indicating foreign objects. The advantage of this process lies in the fact that disturbed picture information which only relates to a single pixel can be separated out and ignored or discarded, since such signals are more likely to be caused by noise or a specific geometrical irregularity of the bale surface.

Finally FIG. 1 shows that polarization filters 74 and 76 can be arranged in front of the video camera 32 or in the field of illumination of the illuminating means 30 in order to increase the contrast between the foreign fibers and the desired cotton fibers. These polarization filters 74, 76 can naturally be rotatably or interchangeably executed, so that the surface can be investigated with or without polarized light and with different angles of the polarized light to obtain the best contrast between, for example, cotton fiber surfaces and foreign object surfaces.

Figure 2:
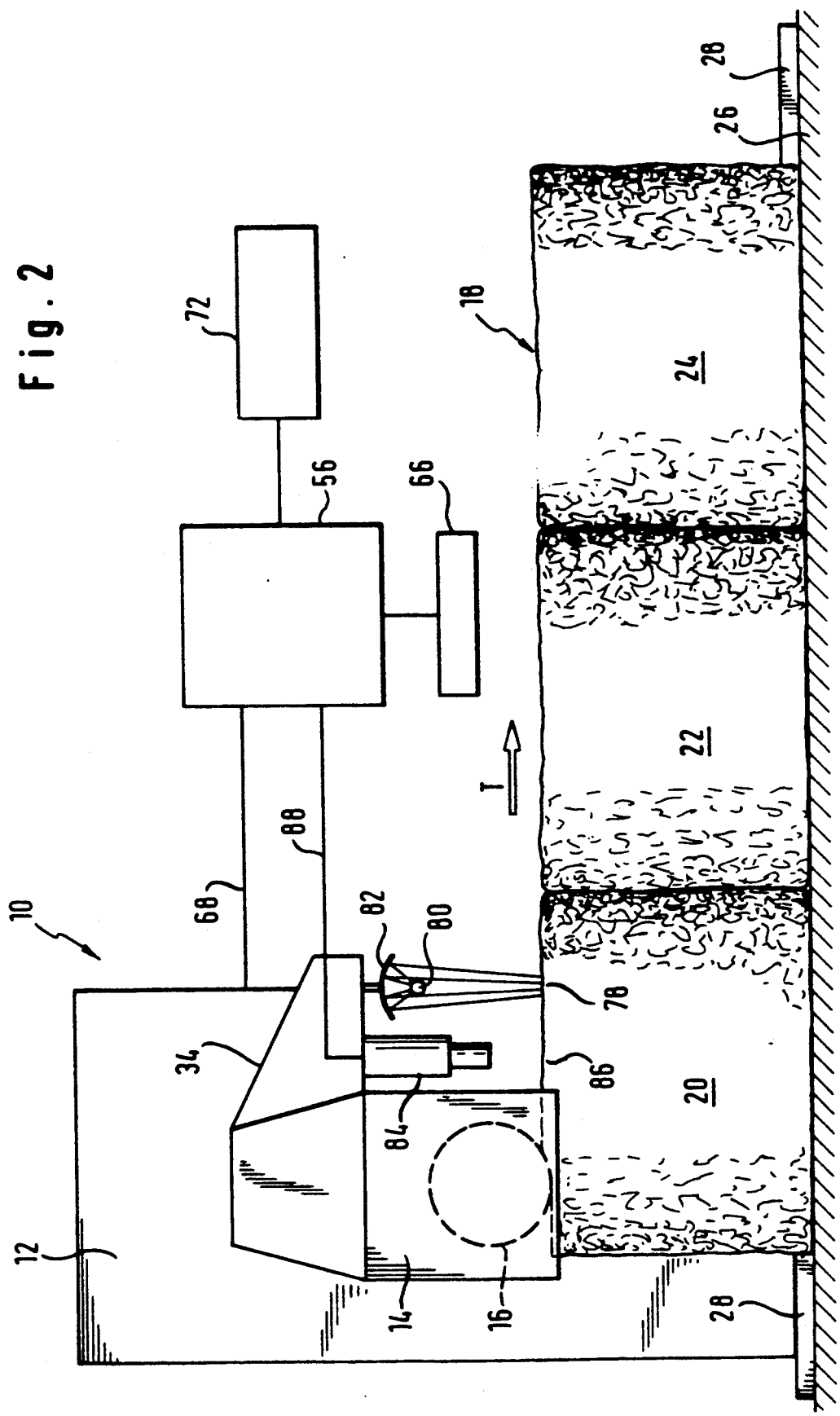
FIG. 2 is a side view of a bale opening machine in accordance with FIG. 1, however with a scanning device in the form of an ultrasonic transmitter/receiver.

FIG. 2 shows a comparable arrangement, and parts which can also be found in FIG. 1 are designated by the same reference numerals. For the sake of brevity only those parts will be especially described here which differ from the embodiment of FIG. 1. The embodiment of FIG. 2 operates with a thermal image of the surface. For this purpose the surface is heated in a region 78 by an infrared bar which extends along the focal line of a thermally reflective concave mirror 82. In this way a restricted strip region of the surface is heated up (e.g., increased 10° to 30° C.) As the bale opening machine moves past, the heated region 78 continuously moves along the surface of the row of bales, with previously heated parts of the surface cooling down.

The thermal camera 84 picks up the thermal distribution along a strip-like region 86 after this surface has cooled to a certain degree. As the cooling of the foreign fibers and the foreign foils takes place in a different manner from the cooling of the cotton fibers (e.g., the different manner can be a known relationship or can be empirically determined), different temperatures arise in the region 86 which are clearly visible in the thermal image. Thus the areal proportions of the regions with differing temperature (e.g., relative to an average temperature of the bale) can be found and can be used as a measure for the degree of the contamination.

For this purpose the signals of the thermal camera 84 are read into computer 56 via a line 88 and the result of the investigation is printed out with the printer 72. Here also a keyboard 66 is used to feed in information concerning the individual bales and the line 68 ensures that the position information is transmitted from the tower to the computer 56. The thermal camera 84 can be a known thermal camera or, for example, can be a type of camera in which the thermal distribution along the strip-like region 86 is scanned point by point. Should the field of view of the camera not be sufficient in this example, or in the example of FIG. 1, to detect the entire width of the row of bales, then several cameras can be arranged alongside on another in order to detect the full width of the row of bales.

Finally FIG. 3 also shows a bale opening machine similar to FIGS. 1 and 2 which is why the same reference numerals have been used here for the same parts. The scanning of the bale surface however takes place here by means of ultrasonic waves. For this purpose an ultrasonic transmitter 90 and an ultrasonic receiver 92 are provided, with the ultrasonic transmitter 90 comprising a piezo-electric sound transducer 94 in the focal point of a reflector 96 which generates a sound field. The sound receiver likewise consists of a piezo-electric converter which is located in the focal point of a reflector 100.

The sound waves emerging from the piezo-electric converter 94 are directed by the reflector 96 in the direction of the surface region 102 of the row of bales and reflected there, with the reflected radiation being concentrated by the reflector 100 onto the piezo-electric converter 98. As it is difficult to generate a sound field over the entire width of the bale row, the transmitter and the receiver 92 are mounted on a yoke-like waggon 104 which can move along two guide bars 106, 108 at the same time, with the guide bars being carried by the structure 34. The signals of the piezo-electric converters 94 and 98 are controlled or received via non-illustrated lines from a computer and are evaulated there in order to obtain information concerning the presence of an abnormally reflecting region of the surface. For example, because many contaminants are more dense (i.e., harder) than fiber materials such as cotton, high amplitude fluctuations of reflected ultrasonic waves associated with the contaminants can be distinguished from relatively low amplitude fluctuations associated with fiber materials.

The signal processing can, for example, take place as indicated in the Swiss patent application CH 03803/88-4, the disclosure of which is hereby incorporated by reference in its entirety. For example, as described in Swiss Patent Application CH 03803/88-4, variations in the time of the envelopes of a subsonic signal for interaction of a material with an ultrasonic field can be detected. In an exemplary embodiment, the frequency of the ultrasonic signal is 98 kHz, and the wavelength of 3.5 mm corresponds to a string diameter but exceeds the diameter of cotton fibers by a factor of approximately 100. Consequently, a flat ultrasonic attenuation occurs with the passage of pure cotton flock while the string produces a peaky patterning in the envelope. The pure cotton flock is clearly distinguishable from the peaky pattern of the string when cotton flock is mixed with string. Thus, a distinction between wanted and unwanted materials can be made using an ultrasonic signal having a frequency of 98 kHz.

The exact wave length and frequency of the transmitted signal should depend on the dimension of the unwanted material. For example, a wavelength range of 0.1 to 3 mm constitutes a usable range for the unwanted material discussed above. A possible range of wavelengths for the transmitted signal in an exemplary embodiment might therefore correspond to 0.1 to 10 mm. However, because cotton fiber dimensions are typically 10 microns, a more preferred wavelength range for the transmitted signal would be approximately 0.1 to 1 mm, which corresponds to a signal having a frequency of approximately 1 Khz.

In a preferred method of measuring the interaction of an ultrasonic field with the material in a bale, a pulsed wave source can be used rather than a continuous wave source as in the case above. In this embodiment, short ultrasonic wave trains are used instead of signals whose amplitudes remain constant. The wave trains are reflected by the material and echo signals are either received by the transmitter or detected by a second ultrasonic receiver and processed in a signal processor. Using the time delay between the ultrasonic pulse transmitted and the echo received by the receiver, a correlator can calculate the distance of the sound-reflecting material from the transducers. If required, image pattern recognition means present in the correlator can detect the unwanted material and produce corresponding signals. For example, the correlator could use the signal detected by the receiver to recognize the intensity or magnitude of the reflected echo. The reflected pulse must, however, be scaled to account for the distance of the particle from the detector. Accordingly, the correlator uses time delay between the transmitted signal and the reflected echo to determine this distance and thus properly proportion the reflected echo.

To distinguish materials such as cotton flock from materials such as a tightly braided string, pattern recognition methods can be used to detect the presence of acoustically dense, unwanted material such as string and fabric in the loose flock flow or fleece. However, since the flow must be continuously monitored laterally, either a large number of measuring facilities disposed one beside another are necessary or a test beam must be guided laterally over the flow or fleece (i.e., a scanning technique.

In all examples a linewise scanning of the entire exposed surface of the row of bales takes place as a result of the movement of the tower along the of row bales in the direction of the arrow T. As shown in FIG. 3 a displacement of the scanning device also takes place along the row. One thus endeavors to scan the entire surface of the row of bales. At the end of the row of bales the tower 12 either moves back in order to subsequently remove further layers of the row of bales or of the individual bales, or a further row of bales is erected on the other side of the rails 28 and is worked off during the return movement of the tower. For this purpose the tower 12 is made rotatable in manner known per se.

A further possibility exists, instead of the above mentioned return movement, of likewise removing fiber material during the return movement of the tower without rotating the tower. The scanning means can either be switched off during this return movement or can also scan the surface of the row of bales. Although this admittedly leads to the same surface being scanned twice, this is however not disturbing. Indeed the double detection can be effectively exploited, for example, in that the surface can be illuminated from a different direction which can lead to the finding of previously "hidden" foreign fibers. Scanning can also be carried out of left hand side of the row of bales in the one direction and of the right hand side of the row of bales in the return movement (or vice versa). For this purpose the scanning means must merely be made displaceable so that it can be displaced along the arm for scanning o both sides of the row of bales. An arrangement of this kind would lead to a finer resolution of the scanned surface.

Furthermore, it is possible to arrange scanning devices on both sides of the arm and either to operate them simultaneously or alternately depending on the direction of travel. With double detection of the surface regions statistically established, foreign body values can be averaged.

Further, the degree of contamination can be compared during the bale opening with a previously determined boundary value selected in accordance with the aforedescribed exemplary embodiments, and upon achieving this boundary value, which can be set either for individual bales or for a whole row of bales or both, an indication and/or an alarm is triggered. The indication and/or alarm then provides the operator an opportunity to terminate the bale opening and to investigate more closely and/or change bales which have which have been partly opened.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A method of establishing whether fiber material is contaminated with foreign objects comprising the steps of:
   investigating fiber material delivered in bales during bale opening by moving a bale opener in a first direction over said bales to expose layers of the fiber material, said step of investigating further including the steps of:
   automatically scanning a surface of at least some layers of the fiber material exposed by the bale opener with a scanning apparatus over the exposed layers of the fiber material and producing signals indicative of a degree of contamination of the scanned fiber material, said scanning being performed in a first direction and in a second direction transverse relative to said first direction during opening of the bales;
   and storing the degree of contamination with scanned foreign objects in association to each particular bale scanned.

2. Method in accordance with claim 1, wherein the degree of the contamination is specified by a value corresponding to a number of foreign objects scanned, an extent of the foreign objects and a color of the foreign objects.

3. Method in accordance with claim 2, wherein the scanning of the surfaces which are laid free is carried out with a scanning device mounted on a tower or arm of a bale opening machine, with the scanning device being mounted in an opening direction in front of an opening member housed in the arm.

4. Method in accordance with claim 3, wherein said step of scanning is performed on an electro-optical basis.

5. Method in accordance with claim 4, wherein said step of scanning further includes a step of photographing and measuring the surface of the exposed layers of fiber material with a video camera, and storing video images which are measured in this way as evidence of the contamination of the bale, in the form of a video film which also carries an identification of the bale.

6. Method in accordance with claim 5, wherein said identification is a bar code.

7. Method in accordance with claim 5, wherein a subsequent manufacturing process in which the fiber material is processed to yarn is carried out by maintaining an association between the fiber material in different processing stages and the respective fiber material bales, such that on finding an increased number of faults during the manufacturing process, the video film associated with the bales from which the yarn is processed can be viewed by an operator to secure proof of contamination.

8. Method in accordance with claim 4, further comprising the step of photographing the surface of exposed layers of fiber material with a video camera, said video camera producing video signals which are electronically processed and evaluated to form foreign object contamination signals.

9. Method in accordance with claim 8, further comprising the step of preparing video recordings from a total surface of a fiber layer during each pass of the bale opening machine wherein removal of a fiber layer occurs.

10. Method in accordance with claim 8, wherein video recordings of a total exposed surface of a fiber layer are only prepared during some passes of the bale opening machine over said bales.

11. Method in accordance with claim 8, wherein the step of photographing further includes a step of substantially uniformly illuminating at least a strip of the surface by the video camera, or the corresponding surface region with diffuse light.

12. Method in accordance with claim 11, wherein the step of illuminating takes place by arranging a fluorescent tube at a focal line of an elongate concave mirror which extends over a width of the bales with the fluorescent tube or the focal line of the elongate concave mirror lying transverse to the bale and in a horizontal plane.

13. Method in accordance with claim 12, wherein the elongate concave mirror is a cylindrical mirror.

14. Method in accordance with claim 12, wherein the elongate concave mirror is a parabolic mirror.

15. Method in accordance with claim 12, wherein the fluroescent tube has a spectral beam distribution which extends from at least 400 nm to 700 nm into an infrared region and into a UV-region, and wherein the video camera has three recording devices for different spectral regions.

16. Method in accordance with claim 15, wherein said spectral regions include the blue, green and red spectral regions.

17. Method in accordance with claim 15, wherein the video signals of the three recording devices are separately evaluated.

18. Method in accordance with claim 17, further comprising a step of changing or specifying a state of polarization of light radiated from the fluorescent tube and received by the video camera.

19. Method in accordance with claim 1, wherein the step of scanning an exposed surface of the layers of fiber material is effected ultrasonically using an ultrasonic device carried by a bale opening machine.

20. Method in accordance with claim 1, wherein said step of scanning further includes the steps of:
heating the exposed surface of the layers of fiber material with infrared radiation; and,
preparing a thermal image of the surface from which the degree of contamination is determined by identifying areas of the image having a proportional temperature which is elevated or reduced relative to a temperature of the fiber material.

21. Method in accordance with claim 1, wherein said step of scanning further includes the steps of:
heating the exposed surface of the layers of fiber material with microwave energy; and,
preparing a thermal image of the surface from which the degree of contamination is determined by identifying areas of the image having a proportional temperature which is elevated or reduced relative to a temperature associated with a greatest portion of the fiber material.

22. Method in accordance with claim 1, wherein the degree of contamination is compared during the bale opening with a previously determined boundary value, and wherein on achieving this boundary value, either for individual bales or for a whole row of bales, an indication and/or alarm is triggered, so that an operator has the opportunity to terminate the bale opening and to investigate more closely and change bales which have been partly opened.

23. Apparatus for establishing whether a fibrous material is contaminated with foreign objects, comprising:
a scanning device mounted for movement over the bales in a first traveling direction or on a structure disposed adjacent to said bale opening machine for scanning a surface of individual bales of fiber material which is exposed during bale opening to detect foreign objects formed as foreign fibers and pieces of foil such as packaging remnants including jute sack remnants, pieces of plastic foil, cords or bands, rags or cleaning scrim;
means for moving the scanning device in a cross-direction to the traveling direction of the bale opening machine; and
a storage means for storing a result of scanning the individual bales.

24. Apparatus in accordance with claim 23, wherein the scanning device is a video camera and the storage means is a video film.

25. Apparatus in accordance with claim 24, wherein said scanning device includes an illuminating device which uniformly illuminates an exposed surface of said individual bales of fiber material.

26. Apparatus in accordance with claim 25, wherein the illuminating device includes a spectral range of at least approximately 400 nm to approximately 700 nm and which extends into an infrared region and optionally into a UV-region; and wherein the video camera has three recording means which deliver separate video signals for spectral regions blue, green and red.

27. Apparatus in accordance with claim 23, wherein the scanning device is a combined ultrasonic sender/-transmitter.

28. Apparatus in accordance with claim 23, wherein said scanning device includes a heat source for warming up an exposed surface of individual bales of fiber material, and wherein the scanning device prepares a thermal image of the exposed surface.

29. Method for opening a row of bales of fiber material and for identifying a combination level of the fiber material in each opened bale comprising the steps of:
moving a rotating opening member in a first direction along a bale to expose plural layers of fiber material in the bale;
recording a position of the rotating opening member relative to the bale and recording bale identification information;
automatically scanning the exposed layers of the bale in said first direction and in a second direction transverse to said first direction to detect characteristics of an exposed bale surface, said scanning being performed with a scanning apparatus over the exposed layers of the bale for producing signals indicative of the degree of contamination of the scanned fiber material;
analyzing the detected characteristics of the bale surface relative to at least one specified threshold value to measure a contamination level of each exposed bale surface; and recording the contamination level of each exposed bale surface with said opening member position and said bale identification information.

30. Method according to claim 29, wherein the step of scanning is performed by optically imaging the exposed layers.

31. Method according to claim 29, wherein the step of scanning further includes the steps of:
emitting ultrasonic sound waves from a tower supporting said rotating opening member; and
detecting echoes reflected from said exposed layers of the bale.

32. Apparatus for opening bales of fiber material and for identifying a contamination level of the fiber material in each opened bale comprising:
a bale opening machine having a tower movable in a first direction along a row of bales, said movable tower supporting a rotating cutting member engageable with the bales for exposing layers of fiber material;
scanning means supported on said movable tower for scanning said exposed layers of fiber material along said first direction and in a second direction transverse to said first direction, said scanning means including at least one signal emitter and one signal receiver for detecting characteristics of an exposed bale surface;
processing means for analyzing the detected characteristics of the exposed bale surface relative to at least one specified threshold value to identify a contamination level of each exposed bale surface; and
recording the contamination level of each exposed bale surface with said opening member position and said bale identification information.

33. Apparatus according to claim 32, wherein said scanning means is supported on said tower in an advanced position relative to said rotating opening member when said rotating opening member is moved in said first direction.

34. Apparatus according to claim 32, wherein said scanning means includes an optical imaging means for recording an image of said exposed layers and bale identification information.

35. Apparatus according to claim 34, wherein said scanning means includes a fluorescent tube located at a focal line of a concave mirror for illuminating a width of a bale being opened, said focal line being situated transverse to said first direction along the width of the bale being opened; and
polarization filters for polarizing light from said fluorescent tube.

36. Apparatus according to claim 32, wherein said scanning means includes an ultrasonic scanning device mounted on said movable tower for emitting ultrasonic waves from said tower and for detecting echoes reflected from said exposed layers.

37. Apparatus according to claim 35, wherein said optical imaging means is a video camera for producing a video signal which contains pixel information, each of said pixels corresponding to a precise unit of area of the illuminated bale surface.

38. Apparatus according to claim 36, wherein said ultrasonic scanning device includes an ultrasonic transmitter and an ultrasonic receiver mounted on a yoke-like wagon for movement in said second direction.

* * * * *